(12) United States Patent
Gorte et al.

(10) Patent No.: US 7,220,343 B2
(45) Date of Patent: May 22, 2007

(54) SOLID-STATE ELECTROCHEMICAL NO$_x$ SENSORS

(75) Inventors: Raymond J. Gorte, Narberth, PA (US);
John M. Vohs, Newtown Square, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/425,556

(22) Filed: Jun. 21, 2006

(65) Prior Publication Data
US 2007/0080061 A1    Apr. 12, 2007

Related U.S. Application Data

(60) Provisional application No. 60/692,242, filed on Jun. 21, 2005.

(51) Int. Cl.
*G01N 27/407*    (2006.01)
(52) U.S. Cl. .................... 204/424; 205/781; 73/23.31
(58) Field of Classification Search ............... 204/424, 204/426; 205/781, 783.5; 73/23.31
See application file for complete search history.

(56) References Cited

U.S. PATENT DOCUMENTS 4,885,078 A * 12/1989 Spengler et al. ............ 204/424
5,698,267 A * 12/1997 Friese et al. ............. 427/430.1
5,716,507 A * 2/1998 Tanaka et al. ............. 204/424
6,468,407 B2   10/2002 Clyde et al.

FOREIGN PATENT DOCUMENTS

JP       2001-99810      * 4/2004

OTHER PUBLICATIONS

Figueiredo, F.M. et al., Reaction between a zirconia-based electrolyte and LaCoO$_3$-based elctrode materials, Solid State Ionics, 1997, pp. 343-349, vol. 101-103.
Di Bartolomeo, E. et al., Zirconia-Based Electrochemical NO$_x$ Sensors with Semiconducting Oxide Electrodes, Journey of the American Ceramic Society, 2004, pp. 1883-1889, vol. 87-10.
Martin, L.P. et al., Electrochemical NO$_x$ Sensors for Automotive Diesel Exhaust, Materials Research Society Symp. Proc., 2003, pp. EE11.3.1-EE11.3.6, vol. 756.
Di Bartolomeo, E. et al., Planar electrochemical sensors based on tape-cast YSZ layers and oxide electrodes, Solid State Ionics, 2004, pp. 173-181, vol. 171.
Lu, G. et al., Stabilized zirconia-based sensors using WO$_3$ electrode for detection of NO or NO$_2$, Sensors and Actuators B, 2000, pp. 125-127, vol. 65.
Skelton, D.C. et al., Suppression of Nitrogen Oxide Dissociation by Gold on Pt(335), J. Phys. Chem. B, 2001, pp. 204-209, vol. 105-1.

* cited by examiner

*Primary Examiner*—Kaj K. Olsen
(74) *Attorney, Agent, or Firm*—Hunton & Williams LLP

(57) ABSTRACT

The embodiments generally relate to porous electrodes for use in solid-state NOx sensors, whereby the electrodes are comprised primarily of ceramic material and electronically conducting material. The electrodes are prepared by impregnating a porous ceramic material with precursors to the electronically conducting material.

7 Claims, 2 Drawing Sheets

SOLID-STATE ELECTROCHEMICAL NO$_X$ SENSORS

This application claims benefit of 60/692,242 filed on Jun. 21, 2005.

FIELD OF THE INVENTION

Embodiments relate generally to solid-state electrochemical NOx sensors, and to methods of their preparation. Specifically, the invention relates to porous NOx electrodes and to methods of producing them whereby the electrodes are prepared from a porous material impregnated with an electron-conducting material to form a porous electrode.

DESCRIPTION OF RELATED ART

Increasingly stringent pollution standards for emissions from fossil fuel combustion processes, particularly internal combustion engines, have spurred research and development into advanced combustion and emissions control technologies. Of particular importance is the emission of nitrogen oxides ("NOx"), for example, from internal combustion engines used to power automobiles. To decrease the emission of NOx from automobile engines and other combustion processes, efficient and durable NOx sensors are desired for in-situ monitoring of emissions and feedback to combustion control systems. NOx sensors are especially valuable for use in the new lean-burn engine systems that are being developed to improve automotive fuel efficiency.

One sensor suggested for measuring the concentration of NOx in a gas stream is an electrochemical (i.e. potentiometric) sensor. In an electrochemical sensor, the following set of electrochemical reactions occurs at the cathode (sensing electrode) and anode (reference electrode), respectively, of the electrochemical sensor.

$$NO_2 + 2e^- \leftrightarrow O^{2-} + NO \text{ (Cathode)}$$

$$O^{2-} \leftrightarrow \tfrac{1}{2}O_2 + 2e^- \text{ (Anode)}$$

The cathode reaction also may be:

$$2NO + 4e^- \leftrightarrow N_2 + 2O^{2-}$$

The reference electrode (anode) typically will be exposed to a source of oxygen of known concentration such as the ambient atmosphere. The concentration of NOx in the exhaust gas therefore can be determined by measuring the potential between the two electrodes.

There are a number of variations on electrochemical sensors for NOx. The most developed of these concepts relies on a dual-chamber approach in which oxygen is electrochemically pumped, or removed, from the gas mixture using an electrode in a first chamber that is unable to dissociate NO. The gas stream then is passed to a second chamber where NO is measured using a more reactive electrode that is capable of dissociating NO. Oxygen is removed before entering the second chamber because oxygen will provide a false signal for NO$_x$. See, for example, D. C. Skelton, et al., *Journal of Physical Chemistry B*, 105, (2001) 204. The dual chamber sensor typically measures a limiting current, and is not believed to require much selectivity for NO in the electrode, whereas the potentiometric electrodes depend more heavily on NO selectivity.

One advantage of this approach is that the electrodes in the two chambers can be simple metals, such as Pt—Au alloys in the first chamber and Pt in the second. However, while this approach is conceptually simple, Riegle, et al. have pointed out that it is challenging in practice to make these devices work because the large excess of O$_2$ in applications of interest must be efficiently removed prior to the second chamber in order to prevent registering a false signal for NOx.

Another approach involves the use of electrodes that selectively react with NO or NO$_2$ in the presence of O$_2$ and other combustion gases. Among the materials that have been used for these selective electrodes are WO$_3$ (see G. Lu, et al, *Sens. Actuators B*, 65 (2000) 125), mixtures of LaFeO$_3$ and WO$_3$ (see E. De Bartolomeo, et al, *J. Am. Ceram. Soc.*, 87 (2004) 1883; E. De Bartolomeo, et al, *Sol Stat Ionics* 171 (2004) 173), and NiCr$_2$O$_4$ (see P. L. Martin, et al, *Matl. Res. Soc. Symp. Proc.* 756 (2003) 139).

These dual chamber and potentiometric NOx selective electrodes typically are used with a solid-state electrolyte, although other types of electrochemical sensors use different electrolytes. Solid-state electrolytes are advantageous because there is no liquid electrolyte, which eliminates metal corrosion and electrolyte management problems typically associated with the use of liquid electrolytes. Instead, the electrolyte primarily is made from solid ceramic materials that are capable of surviving the high temperature environment typically encountered during sensing of NOx in exhaust gases. Because of the high operating temperatures of exhaust systems, the materials used to fabricate the respective NOx sensor components, including the electrolyte, are limited by their chemical stability in oxidizing and reducing environments, chemical stability of contacting materials, conductivity, and thermomechanical compatibility. Yttria-stabilized zirconia ("YSZ"), a ceramic, ion-conducting material has been proposed as an appropriate material for use as a solid-state electrolyte in NOx sensors (see E. De Bartolomeo, et al., *J. Am. Ceram. Soc.*, 87 (2004) 1883).

Another major challenge in NOx selective sensors is that the electrochemical activity of the sensing electrode must be chosen so as to be selective to NOx compounds only and not to other components in the environment such as oxygen. Therefore, it is generally accepted that the NOx sensing response in potentiometric sensors is strongly dependent on both the microstructure of the electrode and the catalytic properties of the electrode.

It is not a simple matter, however, to vary the composition or structure of solid-state electrodes in order to achieve the desired NOx sensing response. These sensing devices require establishing a three-phase boundary ("TPB"), a line where the gas phase (i.e. the exhaust gas that is to be sampled), the solid-state electrolyte (e.g. YSZ), and the "sensing" catalyst (which must also be electronically conductive) all come together. In order to establish a good TPB with a YSZ electrolyte, the electrode material (e.g., WO$_3$, LaFeO$_3$, or NiCr$_2$O$_4$) must be calcined together with the electrolyte at high temperatures However, many oxides undergo solid-state reactions with YSZ and other electrolyte materials at high temperatures, limiting the choice of materials that can be used. Furthermore, there is a poor coefficient of thermal expansion ("CTE") match between many materials of interest, such as LaFeO$_3$ and YSZ, making the electrodes susceptible to fracture upon temperature cycling encountered in use (see F. M. Figueiredo, et al., *Solid State Ionics*, 101–103, 343 (1997)).

The description herein of advantages and disadvantages of various features, embodiments, methods, and apparatus disclosed in other publications is in no way intended to limit the present invention. Indeed, certain features of the invention may be capable of overcoming certain disadvantages, while still retaining some or all of the features, embodiments, methods, and apparatus disclosed therein.

SUMMARY OF THE INVENTION

It would be desirable to provide a solid-state electrochemical NOx sensor that is inexpensive and reliable. It also would be desirable to provide electrode materials, and methods of preparing the electrode materials, for use in electrochemical NOx sensors whereby the materials can be fabricated at lower temperatures to avoid solid state reactions between the electrode and electrolyte materials. Additionally, a method of preparing an electrode that allows compositional flexibility, together with excellent mechanical properties, is desirable.

A feature of an embodiment of the invention therefore is to provide a solid-state electrochemical NOx sensor that is inexpensive, reliable, and relatively easy to fabricate. An additional feature of embodiments of the invention is to provide porous electrode materials for use in electrochemical NOx sensors, methods of making the porous materials, and methods of making electrodes for use in electrochemical NOx sensors.

In accordance with these and other features of various embodiments, there is provided a solid-state electrochemical NOx sensor comprising a ceramic electrolyte and a porous ceramic material electrode having an electronically conducting material dispersed at least partially within the porous ceramic material. The sensor has improved sensitivity to NOx at equivalent or even lower loading levels of conducting material.

In accordance with an additional feature of an embodiment of the invention, there is provided a solid-state NOx sensor comprising a ceramic electrolyte and an electrode having a porous ceramic material and a semiconducting ceramic selected from $LaMnO_3$, $LaFeO_3$, $LaFe_xCo_{(1-x)}O_3$, $BaFe_xCo_{(1-x)}O3$, and $LaCrO_3$, mixtures thereof, and doped versions of these materials, the materials being dispersed at least partially within the pores. Preferably, the electrode is prepared in accordance with the methods described herein, and has the physical properties described herein In accordance with another feature of an embodiment of the invention, there is provided a method of making a porous electrode for an NOx sensor comprising forming a porous ceramic material, impregnating the porous ceramic material with a solution containing an aqueous salt of an electronically conducting material, and heating the mixture to a temperature low enough to prevent a solid state reaction from taking place between the ceramic material and the electronically conducting material, but high enough to drive off the aqueous solution.

In accordance with yet another feature of an embodiment of the invention, there is provided a method of making a NOx sensor comprising forming a dense ceramic electrolyte layer and two porous ceramic material electrode layers, contacting at least the surface of the porous ceramic material electrode layer that will be the cathode layer, with an aqueous salt solution of an electronically conductive material, and optionally contacting at least the surface of the porous ceramic material electrode layer that will be the anode layer with an aqueous salt solution of an anode material.

These and other features and advantages of the preferred embodiments will become more readily apparent when the detailed description of the preferred embodiments is read in conjunction with the attached drawings.

DETAILED DESCRIPTION OF THE PREFERRED EMBODIMENTS

Figure 1:
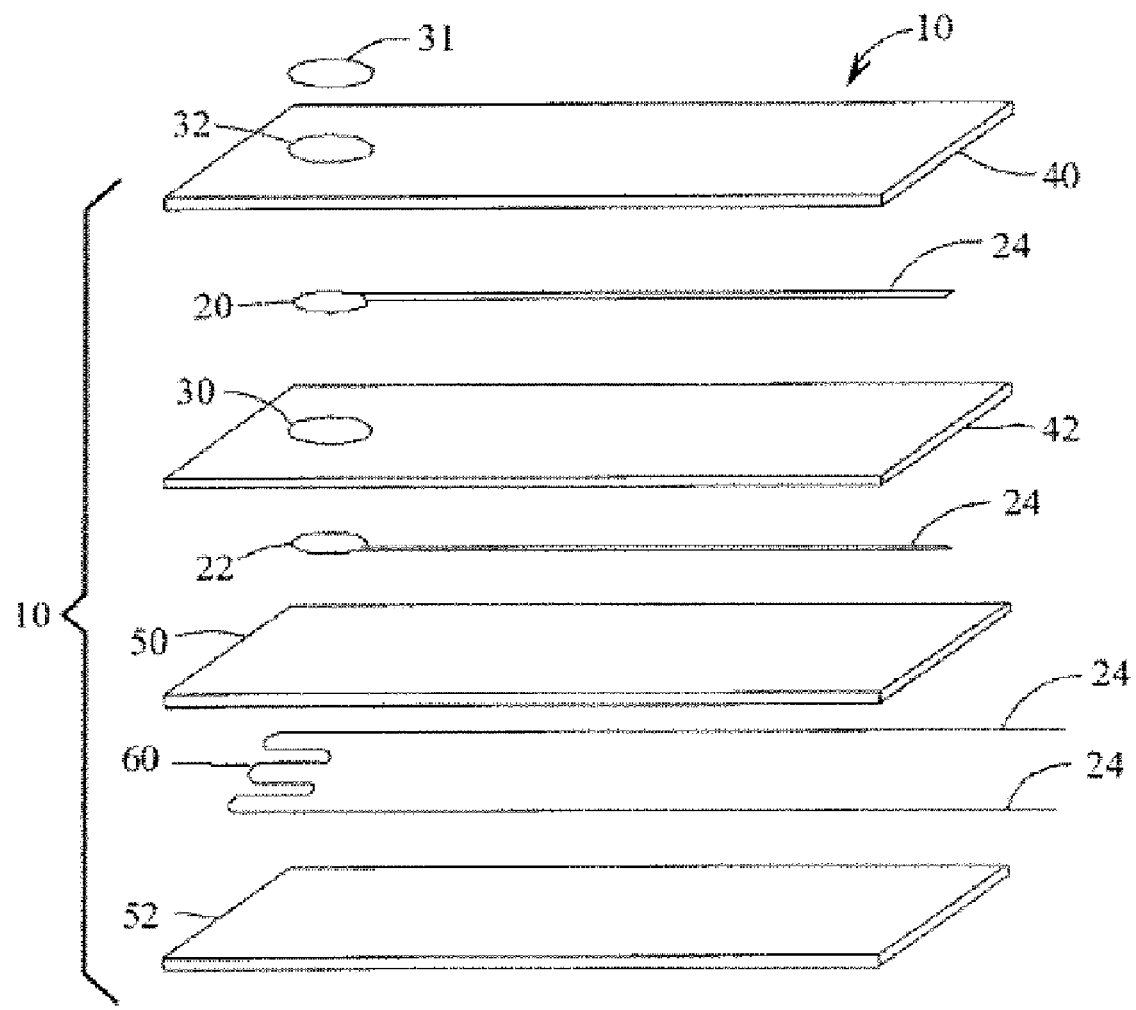
FIG. 1 is an exemplary solid-state NOx sensor.

The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a NOx sensor" is a reference to one or more sensors and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the various anodes, electrolytes, cathodes, and other fuel cell components that are reported in the publications and that might be used in connection with the invention. Nothing herein is to be construed as an admission that the invention is not entitled to antedate such disclosures by virtue of prior invention.

Generally, a solid-state NOx sensor includes a sensing electrode (cathode), a reference electrode (anode), and a solid oxide electrolyte provided between these two electrodes. The anode and cathode generally are porous. The electrolyte may be made of a nonmetallic ceramic, such as dense yttria-stabilized zirconia (YSZ) ceramic, that is a nonconductor of electrons. The two electrodes preferably are connected through a potentiometer. The sensing electrode is exposed to the exhaust gasses. The reference electrode is exposed to a known concentration of oxygen, for example the ambient atmosphere. The components of the solid-state NOx sensor may be arranged in any number of different configurations, in accordance with the guidelines provided herein.

The NOx sensor of the preferred embodiments is not particularly limited to any design of the sensor. Several different designs of NOx sensors have been developed, including, for example, a supported tubular design, a flat plate design, and so forth. For example, U.S. Pat. No. 6,843,900, the disclosure of which is incorporated herein by reference in its entirety, discloses three different designs for a NOx sensor.

In an exemplary design, the NOx sensor may comprise an alumina tube having an interior and an exterior. A cap member may close one end of the tube. The cap member has an interior surface exposed to the interior of the alumina tube and an exterior surface. The cap member may comprise yttria-stabilized zirconia. A first electrode may be disposed on the interior surface of the cap member. Optionally, the first electrode may be covered by zeolite or platinum electrode in the interior of the alumina tube. A second electrode may be disposed on the exterior surface of the cap member.

In another exemplary design, the NOx sensor may comprise a tube having an exterior and an interior. The tube may comprise yttria-stabilized zirconia. A first electrode may be disposed of the exterior of the tube and a second electrode may be disposed on the interior of the tube. A zeolite material or platinum electrode material may cover one of the electrodes, if desired.

In still another exemplary design, the NOx sensor may comprise a substrate of yttria-stabilized zirconia. A first electrode may be disposed on the substrate. A second electrode may be disposed on the substrate. The electrodes may be disposed on the same side of the substrate or may be placed on opposite surfaces of the substrate.

It is preferred that a NOx sensor of the embodiments additionally comprise a source of an electrical potential supplied to the electrodes and a potentiometer in electrical contact with the source of electrical potential. Further, if a zeolite is used, which is not required in the embodiments, it is preferred that the zeolite is Zeolite Y.

In a preferred embodiment, a porous member may shield the substrate and the first and second electrodes from the harsh exhaust gas environment. The porous member may prevent the exhaust gas from directly contacting the substrate and the first and second electrodes. The exhaust gas can come into contact with these elements only after traveling through the porous member. In this way, the porous member may prevent degradation of the sensitive underlying elements such as the substrate, first electrode, and second electrode.

U.S. Pat. No. 6,468,407, the disclosure of which is incorporated herein by reference in its entirety, discloses an exemplary NOx sensor wherein the cathode, and optionally the anode, may be manufactured using the method described herein. FIG. 1 illustrates the exemplary NOx sensor 10.

As shown in FIG. 1, the sensing electrode 20 (to be exposed to the exhaust gasses) and the reference electrode 22 (to be exposed to a known concentration of oxygen, for example, the atmosphere) are positioned on opposite sides of, and adjacent to, an electrolyte layer 30 creating an electrochemical cell (20/30/22). On the side of the exhaust gas electrode 20 opposite solid electrolyte 30 is an optional protective insulating layer 40 with a porous section 32 that enables fluid communication between the exhaust gas electrode 20 and the exhaust gas. A protective coating 31 can be positioned over the porous section 32. The electrolyte 30 and the porous section 32 can be disposed adjacent to, or as inserts within, layers 40 and 42, respectively. Meanwhile, disposed on a side of the reference electrode 22 opposite electrolyte layer 30 may be a heater 60. One or more insulating layers 50 and 52 typically are positioned between the reference gas electrode 22 and the heater 60, as well as on a side of the heater 60 opposite the reference gas electrode 22.

In addition to the above sensor components, conventional components can be employed, including, but not limited to, leads, contact pads, ground plane(s), support layer(s), additional electrochemical cell(s), and the like. The leads 24, which supply current to the heater and electrodes, are typically formed on the same layer as the heater/electrode to which they are in electrical communication and extend from the heater/electrode to the terminal end of the gas sensor where they are in electrical communication with the corresponding via (not shown) and appropriate contact pads (not shown).

Insulating layers 50 and 52, and protective layer 40, provide structural integrity (e.g., protect various portions of the gas sensor from abrasion and/or vibration, and the like, and provide physical strength to the sensor), and physically separate and electrically isolate various components. The insulating layer(s), which can be formed using ceramic tape casting methods or other methods such as plasma spray deposition techniques, screen printing, stenciling and others conventionally used in the art, can each be up to about 200 microns thick or so, with a thickness of about 50 microns to about 200 microns preferred. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating and protective layers is dependent upon the specific electrolyte employed. Typically these insulating layers comprise a ceramic material such as yttria stabilized zirconia (YSZ), alumina, and the like.

Heater 60 is utilized to maintain the sensor element at the desired operating temperature. Heater 60 can be any conventional heater capable of maintaining the sensor end at a sufficient temperature to facilitate the various electrochemical reactions therein. The heater 60, which is typically platinum, aluminum, palladium, and the like, as well as oxides, mixtures, and alloys comprising at least one of the foregoing metals, or any other conventional heater, is generally screen printed or otherwise disposed onto a substrate to a thickness of about 5 microns to about 50 microns.

Using the guidelines provided herein, those skilled in the art will be capable of fabricating a NOx sensor including the inventive electrode having any desired and appropriate configuration. For example, in a potentiometric sensor with a selective electrode, it may not be necessary to separate the anode and cathode into separate compartments. Because NOx sensors are needed for "lean combustion" systems, oxygen typically is present in the environment. A Pt electrode therefore would provide a well-defined potential in that environment and the selective electrode would only need to compare its potential to that well-defined potential. Accordingly, the electrolyte may only need to separate the selective and non-selective electrodes in order to sense the NOx.

The embodiments preferably include a porous electrode, a method of making the electrode, and a NOx sensor containing the electrode, such as the exemplary NOx sensors described herein. The inventive electrode comprises a porous ceramic material, which is an ion conductor, often the same material as that used for the electrolyte, and an electronically conducting material dispersed at least partially within the porous material. The porous ceramic material may include a plurality of pores having a pore size of at least about 0.5 μm. The invention also includes an electrode whereby the cathode has a porosity within the range of from about 10% to about 85%, more preferably 45–80%, and most preferably about 60–75%.

The invention is not particularly limited to any type of ceramic material for use in forming the porous ceramic material. It is preferred that the electrode is comprised of stabilized YSZ impregnated with electronically conducting material. Preferred ceramics for use in the invention include, but are not limited to YSZ, Gd- and Sm-doped ceria (10 to 100 wt %), Sc-doped $ZrO_2$ (up to 100 wt %), doped $LaGaMnO_x$, and other electrolyte materials. These materials preferably are used to form the dense electrolyte layer, and the porous ceramic material electrode precursor layers, although the anode may be fabricated using conventional electrode forming techniques, without resort to the impregnation method described herein for forming the cathode. It is preferred, although not necessary, that the same ceramic material be used to form the electrolyte layer and the porous ceramic material electrode precursor layers.

The electronically conducting material for use in the sensing electrodes of the embodiments includes any of the known electrode materials, as well as any electrode materials later discovered. Materials preferably suitable for use in the invention include composites of $LaMnO_3$, $LaFeO_3$, $LaFe_xCo_{(1-x)}O_3$, $BaFe_xCo_{(1-x)}O3$, and $LaCrO_3$, mixtures thereof, and doped versions of these materials. The invention is not limited to any particular material used for the anode. For example, platinum, palladium, osmium, rhodium, iridium, gold, ruthenium, zirconium, yttrium, cerium, and the like, as well as oxides, mixtures, and alloys comprising at least one of the foregoing catalysts or any other catalyst capable of ionizing oxygen may be used.

It is preferred in the invention that the amount of electronically conducting material in the electrode (cathode or anode) is from about 1% to about 60% by volume, based on the total volume of the electrode, more preferably from about 5% to about 50% by volume, and most preferably from about 15% to about 50% by volume.

The electrodes of the present invention are believed to have increased NOx sensitivity at lower concentrations of the electronically conducting material, when compared to conventional NOx sensors. In addition, the electrodes exhibit percolation behavior at much lower concentrations, when compared to conventional electrodes which is believed to be due to the fact that the conductive phase is not random, but coats the pores of the oxide material. The inventors have shown that, for solid oxide fuel cells, electrodes made by the impregnation method described herein exhibited almost the same conductivity as that of traditional, random mixtures of YSZ with electronically conductive oxides at lower particle loadings of the electronically conductive oxide The inventors now have discovered that the NOx sensors of the embodiments exhibit NOx sensitivity about the same or greater than conventionally prepared NOx sensors, at lower electron conducting material loading.

For the inventive electrodes, the solution of electronically conducting material can be infiltrated throughout the interface of porous YSZ. A nanometer particle layer or a thin film of the conductive phase can be formed relatively homogeneously along the surface of YSZ after sintering, resulting in improved particle-to-particle contact even at low concentration. Therefore the continuous conductive phase can increase the NOx sensitivity, even at lower loading of the electronically conductive material.

The inventive electrodes preferably have a porous structure with a plurality of pores having a pore size greater than about 0.5 μm. Not all the pores need to have a pore size greater than about 0.5 μm, but it is preferred that more than 50%, preferably more than 60% and most preferably more than 75% of the pores have a pore size greater than about 0.5 μm. The pore size is determined by measuring the distance along the major dimension of the pore. It is preferred in the embodiments that a plurality of pores have a pore size greater than about 0.75 μm, more preferably greater than about 1 μm, and even more preferably greater than about 1.5 μm.

The porosity of the electrode prior to dispersing the electronically conducting material typically is about 55 to about 75%. The porosity is measured by immersing the sintered product in water and comparing its weight after immersion with that prior to immersion, as described in Kim, H., et al., *J. Am. Ceram. Soc.*, 85, 1473 (2002). The difference yields the weight of water dispersed in the pores, which when divided by the density will yield the volume of the pores. The porosity then can be determined simply by dividing the volume of the pores by the total volume of the sintered product. Most preferably, the porosity of the sintered electrolyte product prior to dispersing the electronically conducting material is about 60%.

The porosity of the electrode after dispersing the electronically conducting material can be anywhere from about 10% to about 75%, more preferably from about 10% to about 40% and most preferably from about 12% to about 30%. The porosity of the electrode will depend in part on the amount of electronically conducting material used.

Embodiments of the invention further include a method of making the above-described electrode for use in solid-state NOx sensors. In accordance with the method, it is preferred first to form a powder of the electrolyte material, most preferably yttria stabilized zirconia (YSZ), and tape casting the powder and other materials present in a slurry to form a two-layer, green tape of YSZ (one layer for the electrode and the other for the electrolyte). The powder can be mixed together with conventional dispersants, binders, pore formers, and water to form the slurry suitable for tape casting. It is preferred that the slurry used to form the tape for the electrolyte layer contain no pore formers, whereas the slurry used to form the tape for the cathode layer include pore formers to form a porous ceramic material electrode precursor layer. A third layer also may be formed to serve as the anode layer, and tape cast on the opposite side of the electrolyte tape from the cathode tape layer. This layer may be made of similar materials used to form the cathode layer if an impregnation method is utilized to form the anode, or the anode layer may be formed directly by incorporating ionically conductive materials into the anode tape casting slurry.

The two-layer green tape (or optionally three-layer green tape) then preferably is sintered at temperatures within the range of from about 1,200° C. to about 1,800° C., preferably from about 1,350° C. to about 1,650° C., and most preferably from about 1,500° C. to about 1,550° C. to form a porous layer of YSZ near the surface of the dense electrolyte layer, and a dense layer of YSZ from the second layer. Sintering the tape in this manner results in a YSZ wafer having a dense side, approximately 5 μm to about 200 μm thick, supported by a porous layer, approximately 400 μm to about 800 μm thick, more preferably about 600 μm thick.

In an alternative but preferred method, a three layer YSZ structure is fabricated using the above-described method to form a porous, dense material. The optimal thickness of the outer porous electrode layers (cathode and anode) may be within the range of from about 40 microns to about 500 microns.

The electrode preferably is formed by impregnating the porous YSZ portion of the wafer with an aqueous solution containing precursors to the electronically conducting material. For example, the porous YSZ portion can be impregnated with an aqueous solution containing the appropriate concentrations of one or more electronically conductive materials selected from $LaMnO_3$, $LaFeO_3$, $LaCrO_3$, and $LaCoO_3$, and mixtures thereof. For example, preferred salts useful for forming the electrode include saturated, aqueous solutions of $LaMnO_3$, $LaFeO_3$, $LaCrO_3$, and $LaCoO_3$, preferably the nitrate, carbonate, sulfate, and other salts of these materials. The impregnated porous ceramic material then preferably is calcined. The calcination temperature preferably is lower than the temperature at which solid state reactions occur between the oxides of the ion conducting material and the porous ceramic material. Skilled artisans are capable of determining an appropriate calcination temperature, with typical temperatures ranging from about 300° C. to about 650° G.

The conductive phase of the electrode of the embodiments therefore can be formed at relatively low temperatures; temperatures lower than the temperature in which solid state reactions would occur. Thus, the porous ceramic material may be impregnated with the solutions described above, and then the conductive phase formed when the electrode is heated to its operating temperature. This provides a distinct advantage and significant savings in manufacturing costs. These low temperatures also can avoid the appearance of secondary phases but still provide electrodes having a conductive phase that conventionally required sintering at higher temperatures.

Another feature of an embodiment is a NOx sensor that comprises the inventive composite electrode, albeit a cathode or an anode. Preferably, the NOx sensor includes a sensing electrode (cathode), a reference electrode (anode), and a solid oxide electrolyte positioned at least partially between these two electrodes. In a solid-state NOx sensor, the electrolyte is in solid form. Any material now known or later discovered can be used as the electrode material and as the electrolyte material. Typically, the electrolyte is made of a nonmetallic ceramic, such as dense yttria-stabilized zirconia (YSZ) ceramic. Other electrolyte materials useful in the embodiments include Sc-doped $ZrO_2$, Gd- and Sm-doped $CeO_2$, and LaGaMnOx.

The cathode and anode preferably are formed in accordance with the methods described above for forming the electrodes. Alternatively, the anode can be formed by applying the anode composition (e.g., a mixture of YSZ and Pt) as a paste onto the dense side of the wafer and then calcining the electrode at a temperature within the range of from about 1,000° C. to about 1,300° C., more preferably within the range of from about 1,100° C. to about 1,200° C., and most preferably about 1,130° C.

The inventive porous electrodes of the invention, prepared in accordance with the methods described herein, can be used as the cathode or anode material in the NOx sensor. The NOx sensor also includes a potentiometer by which the cathode and anode are connected. By measuring the potential difference between the cathode and anode, and knowing the reference concentration of oxygen (e.g. the atmospheric concentration of oxygen), the concentration of NOx compounds in the exhaust gasses may be determined.

In a preferred embodiment, only the cathode of the solid-state NOx sensor is prepared according to the inventive method wherein the porous ceramic material is impregnated with a solution containing a precursor to an electronically conducting material, and then sintered. Preferably, the anode may be produced by known methods, for example, sintering of a platinum paste on the non-porous electrolyte. Other known methods for production of the anode include sputtering, painting, chemical vapor deposition, screen-printing, and stenciling of other known materials that are capable of ionizing oxygen such as platinum, palladium, osmium, rhodium, iridium, gold, ruthenium, zirconium, yttrium, cerium, calcium, aluminum, silicon, and the like, as well as oxides, mixtures, and alloys comprising at least one of the foregoing catalysts.

The structure of electrodes made by the inventive impregnation procedure is quite different from that of traditional composites. With the impregnated electrodes, the YSZ pore structure may provide a backbone for the electrode and may be very stable since it has been calcined to temperatures as high as 1550° C. together with the electrolyte layer. The electronically conducting materials may "coat" the YSZ pores, resulting in a composite with an ordered, layered structure, rather than a random mixture. Additionally, impregnation of oxide nano-particles may allow the rapid incorporation of well-defined oxide structures.

In addition to compositional flexibility, the inventive process of electrode fabrication has several additional advantages. First, the CTE of composites prepared by impregnation may be much closer to that of YSZ than one would expect for a physical mixture, probably because of the YSZ backbone (see Y. Huang, et al, *J. Electrochem., Soc.,* 151, A646 (2004)). These electrodes therefore may be very stable to thermal cycling in comparison to electrodes made by more conventional methods. Second, these electrodes may be physically strong due to the fact that the YSZ backbone in the electrode has been calcined to high temperatures, together with the electrolyte layer, prior to the addition of the active component. Third, the TPB of these electrodes may be very well established, which is important if the NOx sensors operate in current-limiting mode.

The invention now will be explained with reference to the following non-limiting examples.

EXAMPLES

The inventive process will be applied to produce electrodes using electrode compositions that have been tried in earlier studies to show that the structural characteristics of the impregnated electrodes provide a significantly improved response. For example, electrodes will be produced with $LaFeO_3$, which a review of the literature suggests is one of the more promising materials for NOx sensors.

For the conventional composites, the YSZ and anode material were used as purchased commercially. The YSZ was purchased from Tosoh Corporation, Tokyo, Japan. The anode material could be purchased as is commercially, or fabricated from commercially available components, such as a combination of YSZ and NiO. After dissolving the anode material salts in distilled water and combined with YSZ powder, the mixture was dried and calcined at 800° C. in air overnight. This powder then was ground in a mortar and pestle in the presence of iso-propanol, sintered in air at 1400° C. for 4 h, and then ground again.

To prepare composite electrodes by impregnation, preferably for preparing the cathode materials, a porous YSZ matrix first was prepared using methods described, for example, in Gorte, R. J., et al., *Adv. Materials,* 12, 1465 (2000), Park, S., et al., *J. Electrochem. Soc.,* 148, A443 (2001), and Huang, Y., et al., *J. Electrochem. Soc.,* 151 (4) A646–A651 (2004). The YSZ powder (18.2 g, 8-YSZ, 8 mol % $Y_2O_3$, Tosoh TZ-8Y) was used as received and mixed with 30 g distilled water, a dispersant (1.27 g, Duramax 3005, Rohm & Haas), binders (3.85 g HA12 and 5.73 g B1000, Rohm & Haas), and pore formers (18.3 g. of either graphite (GE, Alfa Aeser, 325 mesh, conductivity grade) or a mixture of graphite and polymethyl methacrylate (PMMA; Scientific Polymer Products, Inc., Mw 540,000)). This slurry was either cast into tapes that would result in porous ceramic wafers, 600 μm thick, or formed into rectangular pieces, 2 mm×2 mm×10 mm. After calcination to 1550° C., the YSZ wafers and rectangular pieces were found to have a porosity of between 60% and 70%, depending on the PMMA:graphite ratio, as shown by the weight change of the sample after water immersion. Kim, H., et al, *J. Am. Ceram. Soc.,* 85, 1473 (2002). The phase and microstructure of selected samples were investigated using Cu Kα X-ray diffraction (XRD) and scanning electron microscopy (SEM: JEOL JSM 6300LV). A SEM showing the microstructure of the porous layer is provided in FIG. 2, embodiment (a).

Figure 2:
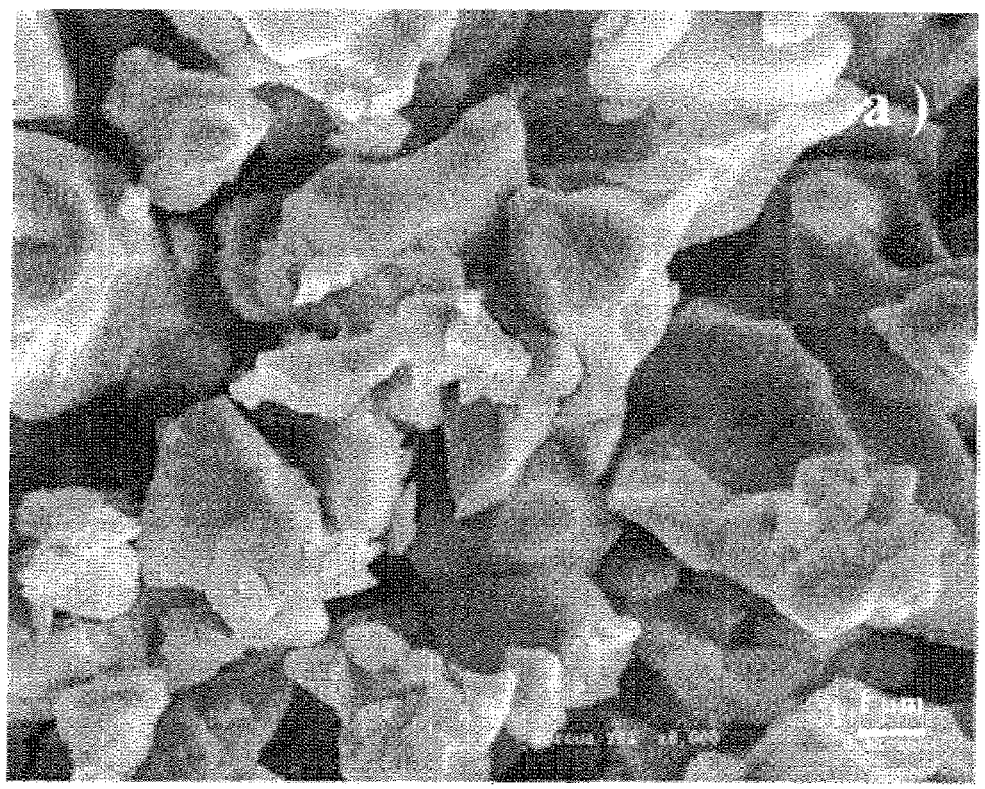
FIG. 2 is an SEM of the microstructure of an initial porous YSZ material (a), and the porous YSZ material impregnated with LSF (b), as described in the examples.
Figure 2:
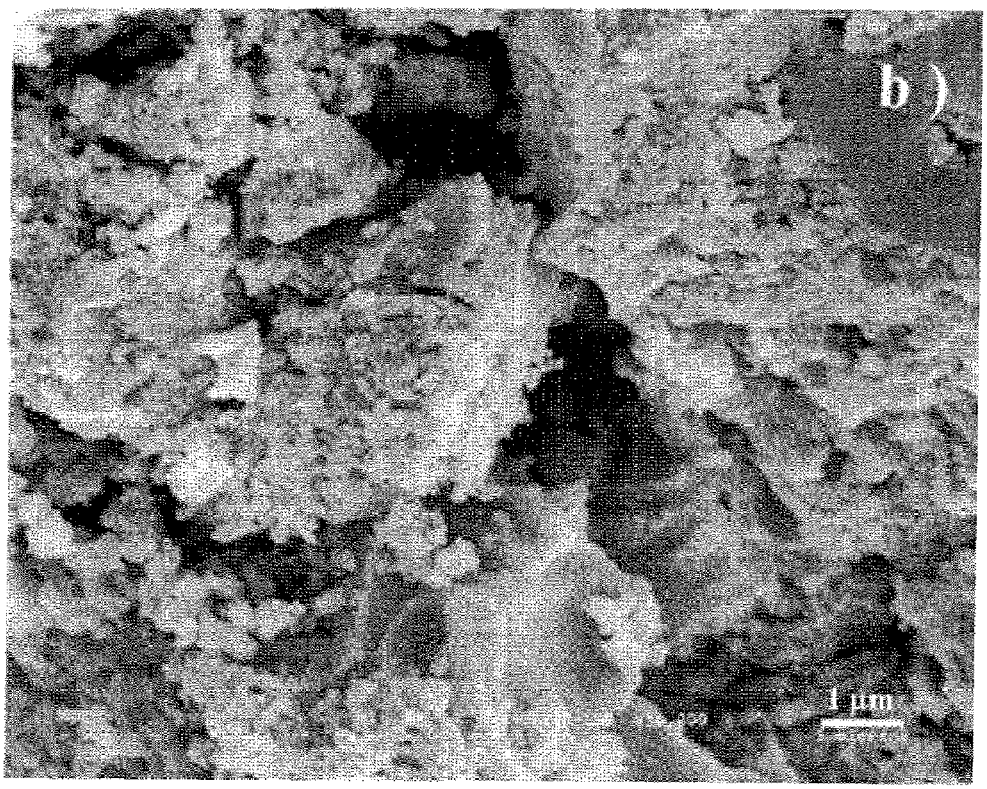

The Sr-doped LaFeO$_3$ (LSF) then was impregnated into the porous YSZ layer prepared above, using aqueous solutions containing La, Sr., and Fe salts. The solutions were prepared by dissolving the nitrate salts [La(NO$_3$)$_3$.6H$_2$O, Alfa Aesar, ACS 99.9%; Sr(NO$_3$)$_2$, Alfa Aesar, ACS 99.0%; and Fe(NO$_3$)$_3$.9H$_2$O, Alfa Aesar, ACS 98+%] in water at a molar ratio of La:Sr:Fe=0.8:0.2"1. After adding citric acid to the point at which the concentration of citrate ions was equal to that of the metal ions, the clear mixture was stirred for 24 hours at 333 K, with water added to make up for that lost by evaporation. The citrate complexes were highly soluble in water, but it was necessary to maintain a low concentration, 1.0 mol of metal ions per liter, to avoid having high viscosities. In order to introduce a sufficient amount of LSF into the YSZ, it was usually necessary to use multiple impregnations and to calcine the impregnated sals to 723 K to remove the citrate and nitrate ions between impregnations. A SEM of the LSF impregnated YSZ is shown in FIG. 2, embodiment (b).

The experimental conditions for testing the response of the sensors will be as close as possible to those used in earlier studies (see, for example, E. De Bartolomeo, et al., *J. Am. Ceram. Soc.*, 87 (2004) 1883) so as to obtain a comparison of performance changes with structure. These experiments will involve measuring the sensor response while switching the gas between a gas mixture containing O$_2$ and inert gases and a similar mixture containing various levels of NO$_2$. A pulse reactor will be used to carry out these switching experiments. The phase and microstructure of selected samples also may be investigated using XRD and Scanning Electron Microscopy (SEM, JEOL JSM-6300LV).

After initial studies with LaFeO$_3$, a series of materials will be examined to determine the sensitivity of the sensors to composition. One series of electronically conducting materials of particular interest includes the perovskites LaMnO$_3$, LaCrO$_3$, and LaCoO$_3$. In addition to determining the effect of composition in the perovskite, the effect of dopants in these materials, especially precious metals and materials that would be expected to form nitrates readily such as SrO and BaO, will be examined. It is expected that these additives will change the reactivity of the perovskite towards NO$_2$, thereby allowing the sensitivity of the sensor to be "tuned" in ways that would not be possible for sensor electrodes prepared by conventional methods.

Exemplary composite electrodes will be made by impregnation of a porous YSZ matrix with precursors to the electronically conductive materials, including LaMnO$_3$, LaCrO$_3$, LaFeO$_3$, and LaCoO$_3$. To prepare composites by impregnation, a porous YSZ matrix first will be prepared using methods described, for example, in Gorte, R. J., et al, *Adv. Materials*, 12, 1465 (2000), and Park, S., et al, *J. Electrochem. Soc.*, 148, A443 (2001). For example, YSZ powder (ZrO$_2$ with 8 mol % Y$_2$O$_3$, Tosoh TZ-84) may be used as received and mixed with distilled water, a dispersant (Duramax 3005, Rohm & Haas), binders (HA12 and B1000, Rohm & Haas), and pore formers (graphite and polymethyl methacrylate). This slurry may be cast into tapes that will result in porous ceramic wafers, or formed into rectangular pieces. After calcination to approximately 1550° C., the porosity of the YSZ wafers and rectangular pieces will be determined as shown by the weight change of the sample after water immersion (see Kim, H., et al, *J. Am. Ceram. Soc.*, 85, 1473 (2002)). An electronically conducting material precursor then will be added to the porous YSZ through impregnation of the YSZ.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A solid-state NOx sensor comprising:
   a ceramic electrolyte; and
   an electrode adjacent the ceramic electrolyte, the electrode being comprised of a porous ceramic material and a semiconducting ceramic material selected from the group consisting of LaMnO$_3$, LaFeO$_3$, LaFe$_x$Co$_{(1-x)}$O$_3$, BaFe$_x$Co$_{(1-x)}$O3, LaCrO$_3$, mixtures thereof, and doped versions of these materials, the materials being dispersed at least partially within the pores of the porous ceramic material.

2. The solid-state NOx sensor as recited in claim 1, wherein the ceramic electrolyte is comprised of yttria-stabilized zirconia (YSZ).

3. The solid-state NOx sensor as recited in claim 1, further comprising a second adjacent the ceramic electrolyte, and positioned on a side of the electrolyte opposite the side of the electrode.

4. The solid-state NOx sensor as recited in claim 1, further comprising an insulating layer positioned adjacent the electrode.

5. The solid-state NOx sensor as recited in claim 1, wherein the porous ceramic material forming the electrode is YSZ.

6. The solid-state NOx sensor as recited in claim 1, wherein the porous ceramic material forming the electrode has more than about 60% of its pores having a pore size greater than about 0.5 µm.

7. The solid-state NOx sensor as recited in claim 1, wherein the semiconducting ceramic material is selected from the group consisting of LaMnO$_3$, LaFeO$_3$, LaCoO$_3$, LaCrO$_3$, mixtures thereof, and doped versions of these materials.

* * * * *